(12) United States Patent
Adanny et al.

(10) Patent No.: US 10,322,296 B2
(45) Date of Patent: *Jun. 18, 2019

(54) METHOD AND APPARATUS FOR FRACTIONAL SKIN TREATMENT

(71) Applicant: SYNERON MEDICAL LTD., Yoqneam Illit (IL)

(72) Inventors: Yossef Ori Adanny, Mitzpe (IL); Genady Nahshon, Binyamina (IL); Baruch Levine, Afula (IL); Avner Rosenberg, Beit-Shearim (IL)

(73) Assignee: Syneron Medical Ltd., Yoqneam Illit (IL)

( * ) Notice: Subject to any disclaimer, the term of this patent is extended or adjusted under 35 U.S.C. 154(b) by 335 days.

This patent is subject to a terminal disclaimer.

(21) Appl. No.: 14/791,840

(22) Filed: Jul. 6, 2015

(65) Prior Publication Data
US 2015/0297283 A1 Oct. 22, 2015

Related U.S. Application Data

(63) Continuation of application No. 14/252,832, filed on Apr. 15, 2014, now Pat. No. 9,072,882, which is a
(Continued)

(51) Int. Cl.
*A61B 18/14* (2006.01)
*A61N 5/00* (2006.01)
(Continued)

(52) U.S. Cl.
CPC ............ *A61N 5/00* (2013.01); *A61B 18/1233* (2013.01); *A61B 18/14* (2013.01); *A61B 18/18* (2013.01); *A61N 1/0476* (2013.01); *A61N 1/08* (2013.01); *A61B 2018/0016* (2013.01); *A61B 2018/0047* (2013.01); *A61B 2018/00452* (2013.01);
(Continued)

(58) Field of Classification Search
CPC ..... A61B 18/1233; A61B 18/14; A61B 18/18; A61B 2018/0016; A61B 2018/00452; A61B 2018/0047; A61B 2018/0577; A61B 2018/00589; A61B 2018/00642; A61B 2018/00702; A61B 2018/00827; A61B 2018/00875; A61B 2018/1467;
(Continued)

(56) References Cited

U.S. PATENT DOCUMENTS 4,200,104 A 4/1980 Harris
4,844,063 A 7/1989 Clark
(Continued)

FOREIGN PATENT DOCUMENTS

AU 200017948 5/2003
AU 199964868 1/2005
(Continued)

OTHER PUBLICATIONS

Guidelines for Limiting Exposure to Time-Varying Electric, Magnetic, and Electromagnetic Fields (Up to 300 GHz), International Commission on Non-Ionizing Radiation Protection, ICNIRP Guidelines, Apr. 1998, vol. 74, No. 4, pp. 496-522.

*Primary Examiner* — Michael F Peffley
(74) *Attorney, Agent, or Firm* — Finnegan, Henderson, Farabow, Garrett & Dunner LLP (57) ABSTRACT

An apparatus for cosmetic RF skin treatment where the RF energy supply is isolated from the patient treated, such that in course of treatment no undesired current flows through the subject body.

23 Claims, 7 Drawing Sheets

Related U.S. Application Data continuation of application No. 13/400,434, filed on Feb. 20, 2012, now abandoned, which is a continuation of application No. 12/505,576, filed on Jul. 20, 2009, now Pat. No. 8,357,150.

(51) Int. Cl.
| | | |
|---|---|---|
| *A61N 1/04* | (2006.01) | |
| *A61N 1/08* | (2006.01) | |
| *A61B 18/12* | (2006.01) | |
| *A61B 18/18* | (2006.01) | |
| *A61B 18/00* | (2006.01) | |
| *A61B 18/16* | (2006.01) | |

(52) U.S. Cl.
CPC .............. *A61B 2018/00577* (2013.01); *A61B 2018/00589* (2013.01); *A61B 2018/00642* (2013.01); *A61B 2018/00702* (2013.01); *A61B 2018/00827* (2013.01); *A61B 2018/00875* (2013.01); *A61B 2018/1467* (2013.01); *A61B 2018/162* (2013.01); *A61B 2018/165* (2013.01)

(58) Field of Classification Search
CPC ........ A61B 2018/162; A61B 2018/165; A61N 1/0476; A61N 1/08
See application file for complete search history.

(56) References Cited

U.S. PATENT DOCUMENTS

| | | |
|---|---|---|
| 5,287,380 A | 2/1994 | Hsia |
| 5,312,395 A | 5/1994 | Tan et al. |
| 5,319,363 A | 6/1994 | Welch et al. |
| 5,320,618 A | 6/1994 | Gustafsson |
| 5,360,425 A | 11/1994 | Cho |
| 5,383,874 A | 1/1995 | Jackson et al. |
| 5,394,492 A | 2/1995 | Hwang |
| 5,598,426 A | 1/1997 | Hsia et al. |
| 5,599,342 A | 2/1997 | Hsia et al. |
| 5,681,282 A | 10/1997 | Eggers et al. |
| 5,755,753 A | 5/1998 | Knowlton |
| 5,766,153 A | 6/1998 | Eggers et al. |
| 5,789,755 A | 8/1998 | Bender |
| 5,814,040 A | 9/1998 | Nelson et al. |
| 5,820,626 A | 10/1998 | Baumgardner |
| 5,873,855 A | 2/1999 | Eggers et al. |
| 5,885,274 A | 3/1999 | Fullmer et al. |
| 5,968,034 A | 10/1999 | Fullmer et al. |
| 5,971,982 A | 10/1999 | Betsill et al. |
| 5,976,123 A | 11/1999 | Baumgardner et al. |
| 5,979,454 A | 11/1999 | Anvari et al. |
| 5,983,135 A | 11/1999 | Avrahami |
| 6,024,733 A | 2/2000 | Eggers et al. |
| 6,026,816 A | 2/2000 | McMillian et al. |
| 6,028,316 A | 2/2000 | Bender |
| 6,059,772 A | 5/2000 | Hsia et al. |
| 6,117,335 A | 9/2000 | Bender |
| 6,120,497 A | 9/2000 | Anderson et al. |
| 6,132,426 A | 10/2000 | Kroll |
| 6,148,232 A | 11/2000 | Avrahami |
| 6,171,301 B1 | 1/2001 | Nelson et al. |
| 6,200,308 B1 | 3/2001 | Pope et al. |
| 6,200,466 B1 | 3/2001 | Bender |
| 6,235,015 B1 | 5/2001 | Mead, III et al. |
| 6,248,103 B1 | 6/2001 | Tannenbaum et al. |
| 6,273,885 B1 | 8/2001 | Koop et al. |
| 6,277,116 B1 | 8/2001 | Utely et al. |
| 6,328,033 B1 | 12/2001 | Avrahami |
| 6,364,872 B1 | 4/2002 | Hsia et al. |
| 6,402,742 B1 | 6/2002 | Blewett |
| 6,413,253 B1 | 7/2002 | Koop et al. |
| 6,413,255 B1 | 7/2002 | Stern |
| 6,440,121 B1 | 8/2002 | Weber et al. |
| 6,451,007 B1 | 9/2002 | Koop et al. |
| 6,512,782 B1 | 1/2003 | Hsia et al. |
| 6,514,241 B1 | 2/2003 | Hsia et al. |
| 6,514,244 B2 | 2/2003 | Pope et al. |
| 6,547,786 B1 | 4/2003 | Goble |
| 6,597,946 B2 | 7/2003 | Avrahami et al. |
| 6,605,080 B1 | 8/2003 | Altshuler et al. |
| 6,607,498 B2 | 8/2003 | Eshel |
| 6,611,706 B2 | 8/2003 | Avrahami et al. |
| 6,615,079 B1 | 9/2003 | Avrahami |
| 6,659,999 B1 | 12/2003 | Anderson et al. |
| 6,662,054 B2 | 12/2003 | Kreindel et al. |
| 6,702,808 B1 | 3/2004 | Kreindel |
| 6,708,060 B1 | 3/2004 | Avrahami et al. |
| 6,711,435 B2 | 3/2004 | Avrahami |
| 6,743,222 B2 | 6/2004 | Durkin et al. |
| 6,749,624 B2 | 6/2004 | Knowlton |
| 6,761,826 B2 | 7/2004 | Bender |
| 6,829,260 B2 | 12/2004 | Hsia et al. |
| 6,889,090 B2 | 5/2005 | Kreindel |
| 6,939,344 B2 | 9/2005 | Kreindel |
| 7,022,121 B2 | 4/2006 | Stern et al. |
| 7,041,100 B2 | 5/2006 | Kreindel |
| 7,060,061 B2 | 6/2006 | Altshuler et al. |
| 7,062,317 B2 | 6/2006 | Avrahami et al. |
| 7,094,252 B2 | 8/2006 | Koop |
| 7,122,029 B2 | 10/2006 | Koop et al. |
| 7,123,957 B2 | 10/2006 | Avrahami |
| 7,164,942 B2 | 1/2007 | Avrahami et al. |
| 7,184,614 B2 | 2/2007 | Slatkine |
| 7,217,265 B2 | 5/2007 | Hennings et al. |
| 7,238,183 B2 | 7/2007 | Kreindel |
| 7,241,491 B2 | 7/2007 | Kreindel et al. |
| 7,331,951 B2 | 2/2008 | Eshel et al. |
| 7,333,698 B2 | 2/2008 | Israel |
| 7,335,377 B2 | 2/2008 | Stern et al. |
| 7,347,855 B2 | 3/2008 | Eshel et al. |
| 7,363,075 B2 | 4/2008 | Stern et al. |
| 7,383,084 B2 | 6/2008 | Stern et al. |
| 7,395,111 B2 | 7/2008 | Levin et al. |
| 7,415,306 B2 | 8/2008 | Levin et al. |
| 7,435,247 B2 | 10/2008 | Woloszko et al. |
| 7,494,488 B2 | 2/2009 | Weber |
| 7,524,316 B2 | 4/2009 | Hennings et al. |
| 7,558,625 B2 | 7/2009 | Levin et al. |
| 7,637,906 B2 | 12/2009 | Koop et al. |
| 7,643,883 B2 | 1/2010 | Kreindel |
| 7,644,715 B2 | 1/2010 | Hayes et al. |
| 7,662,404 B2 | 2/2010 | Stern et al. |
| 7,671,327 B2 | 3/2010 | Clancy et al. |
| 7,709,997 B2 | 5/2010 | Nudelman et al. |
| 7,740,651 B2 | 6/2010 | Barak et al. |
| 7,762,965 B2 | 7/2010 | Slatkine |
| 7,815,570 B2 | 10/2010 | Eshel et al. |
| 7,824,394 B2 | 11/2010 | Manstein |
| 7,857,775 B2 | 12/2010 | Rosenberg et al. |
| 7,875,023 B2 | 1/2011 | Eshel et al. |
| 7,891,362 B2 | 2/2011 | Domankevitz et al. |
| 7,921,854 B2 | 4/2011 | Hennings et al. |
| 7,935,139 B2 | 5/2011 | Slatkine |
| 7,947,304 B2 | 5/2011 | Sacks et al. |
| 7,955,262 B2 | 6/2011 | Rosenberg |
| 8,007,493 B2 | 8/2011 | McGill et al. |
| 8,016,810 B2 | 9/2011 | Levin et al. |
| 8,041,421 B2 | 10/2011 | Birchall et al. |
| 8,127,771 B2 | 3/2012 | Hennings |
| 8,133,191 B2 | 3/2012 | Rosenberg et al. |
| 8,133,216 B2 | 3/2012 | Knopp et al. |
| 8,133,505 B2 | 3/2012 | Stern et al. |
| 8,135,475 B2 | 3/2012 | Kreindel et al. |
| 8,142,426 B2 | 3/2012 | Knopp et al. |
| 8,216,215 B2 | 7/2012 | Flyash et al. |
| 8,246,611 B2 | 8/2012 | Paithankar et al. |
| 8,256,429 B2 | 9/2012 | Hennings et al. |
| 8,273,037 B2 | 9/2012 | Kreindel et al. |
| 8,273,080 B2 | 9/2012 | Mehta |
| 8,276,590 B2 | 10/2012 | Hennings et al. |
| 8,277,495 B2 | 10/2012 | Demetriou et al. |
| 8,281,675 B2 | 10/2012 | Levin et al. |
| 8,328,795 B2 | 12/2012 | Domankevitz et al. |

(56) References Cited

U.S. PATENT DOCUMENTS

| | | |
|---|---|---|
| 8,337,493 B2 | 12/2012 | Sohn |
| D674,485 S | 1/2013 | Flyash et al. |
| 8,357,146 B2 | 1/2013 | Hennings et al. |
| 8,357,150 B2 | 1/2013 | Rosenberg |
| D676,959 S | 2/2013 | Flyash et al. |
| D676,960 S | 2/2013 | Flyash et al. |
| 8,365,741 B2 | 2/2013 | Hennings et al. |
| 8,409,183 B2 | 4/2013 | Hennings et al. |
| 8,419,726 B2 | 4/2013 | Mehta |
| 8,430,104 B2 | 4/2013 | Hennings et al. |
| 8,439,045 B2 | 5/2013 | Hennings et al. |
| 8,448,644 B2 | 5/2013 | Hennings et al. |
| 8,454,540 B2 | 6/2013 | Eshel et al. |
| 8,466,605 B2 | 6/2013 | Kushculey et al. |
| 8,479,624 B2 | 7/2013 | Flyash et al. |
| 8,496,654 B2 | 7/2013 | Rosenberg Avner |
| 8,512,327 B2 | 8/2013 | Knopp et al. |
| 8,516,706 B2 | 8/2013 | Flyash et al. |
| 8,540,705 B2 | 9/2013 | Mehta |
| 8,568,339 B2 | 10/2013 | Rybyanets |
| 8,573,227 B2 | 11/2013 | Hennings et al. |
| 8,579,896 B2 | 11/2013 | Kreindel |
| 8,585,693 B2 | 11/2013 | Knopp et al. |
| 8,606,366 B2 | 12/2013 | Flyash et al. |
| 8,608,737 B2 | 12/2013 | Mehta et al. |
| 8,613,741 B1 | 12/2013 | Jones et al. |
| 8,641,703 B2 | 2/2014 | Flyash et al. |
| 8,685,012 B2 | 4/2014 | Hennings et al. |
| 8,702,769 B2 | 4/2014 | Eckhouse et al. |
| 8,709,011 B2 | 4/2014 | Eckhouse et al. |
| 8,771,263 B2 | 7/2014 | Epshtein et al. |
| 8,771,268 B2 | 7/2014 | Kreindel |
| 8,778,003 B2 | 7/2014 | Eckhouse et al. |
| 8,814,922 B2 | 8/2014 | Hennings et al. |
| 8,906,015 B2 | 12/2014 | Kreindel |
| 8,936,593 B2 | 1/2015 | Epshtein et al. |
| D724,749 S | 3/2015 | Koby et al. |
| 8,979,830 B2 | 3/2015 | Hennings |
| 8,979,833 B2 | 3/2015 | McGill et al. |
| 9,011,419 B2 | 3/2015 | Flyash et al. |
| 9,037,229 B2 | 5/2015 | Bar-El et al. |
| D732,679 S | 6/2015 | Assa et al. |
| D733,310 S | 6/2015 | Assa et al. |
| 9,084,587 B2 | 7/2015 | Eckhouse et al. |
| D735,866 S | 8/2015 | Assa et al. |
| 9,144,463 B2 | 9/2015 | Hennings et al. |
| 9,277,958 B2 | 3/2016 | Schomacker et al. |
| 9,278,230 B2 | 3/2016 | Levin et al. |
| 9,314,293 B2 | 3/2016 | Rosenberg |
| 9,301,588 B2 | 4/2016 | Eckhouse et al. |
| 9,308,046 B2 | 4/2016 | Schomacker et al. |
| 9,381,057 B2 | 7/2016 | Schomacker et al. |
| 9,486,285 B2 | 11/2016 | Paithankar et al. |
| 9,496,678 B2 | 11/2016 | Bhawalkar et al. |
| 9,539,439 B2 | 1/2017 | Jones et al. |
| 9,585,687 B2 | 3/2017 | Tenenbaum et al. |
| 9,597,528 B2 | 3/2017 | Schomacker et al. |
| 9,722,392 B2 | 8/2017 | Bhawalkar et al. |
| 9,889,297 B2 | 2/2018 | Schomacker |
| 9,895,188 B2 | 2/2018 | Schomacker et al. |
| 2004/0210214 A1 | 10/2004 | Knowlton |
| 2006/0036300 A1 | 2/2006 | Kreindel |
| 2006/0047281 A1 | 3/2006 | Kreindel |
| 2006/0241440 A1 | 10/2006 | Eshel et al. |
| 2007/0038201 A1 | 2/2007 | Koop et al. |
| 2007/0073367 A1 | 3/2007 | Jones et al. |
| 2007/0173799 A1 | 7/2007 | Hsia |
| 2007/0191827 A1 | 8/2007 | Lischinsky et al. |
| 2007/0270785 A1 | 11/2007 | Jones et al. |
| 2007/0287949 A1 | 12/2007 | Levin et al. |
| 2007/0292445 A1 | 12/2007 | Levin |
| 2008/0004678 A1 | 1/2008 | Kreindel |
| 2008/0021527 A1 | 1/2008 | Hennings et al. |
| 2008/0091179 A1 | 4/2008 | Durkin et al. |
| 2008/0161888 A1 | 7/2008 | Hisa |
| 2008/0188846 A1 | 8/2008 | Palanker et al. |
| 2008/0214988 A1 | 9/2008 | Altshuler et al. |
| 2008/0215040 A1 | 9/2008 | Paithankar et al. |
| 2008/0221649 A1 | 9/2008 | Echague et al. |
| 2008/0269734 A1 | 10/2008 | Echague et al. |
| 2008/0274166 A1 | 11/2008 | Sacks et al. |
| 2008/0281236 A1 | 11/2008 | Eshel et al. |
| 2008/0281389 A1 | 11/2008 | Koop et al. |
| 2009/0036958 A1 | 2/2009 | Mehta |
| 2009/0054743 A1 | 2/2009 | Stewart |
| 2009/0099483 A1 | 4/2009 | Rybyanets |
| 2009/0105706 A1 | 4/2009 | Livneh |
| 2009/0112205 A1 | 4/2009 | McGill et al. |
| 2009/0171251 A1 | 7/2009 | Rybyanets et al. |
| 2009/0171254 A1 | 7/2009 | Goland et al. |
| 2009/0186318 A1 | 7/2009 | Assa et al. |
| 2009/0187175 A1 | 7/2009 | Assa et al. |
| 2009/0187176 A1 | 7/2009 | Assa et al. |
| 2009/0210766 A1 | 8/2009 | Eckhouse et al. |
| 2009/0221938 A1 | 9/2009 | Rosenberg et al. |
| 2009/0227995 A1 | 9/2009 | Bhawalkar et al. |
| 2010/0004536 A1 | 1/2010 | Rosenberg |
| 2010/0010480 A1 | 1/2010 | Mehta et al. |
| 2010/0010484 A1 | 1/2010 | Mehta et al. |
| 2010/0016846 A1 | 1/2010 | Hennings et al. |
| 2010/0017750 A1 | 1/2010 | Rosenberg et al. |
| 2010/0016727 A1 | 2/2010 | Rosenberg |
| 2010/0016761 A1 | 2/2010 | Rosenberg |
| 2010/0042020 A1 | 2/2010 | Ben-Ezra |
| 2010/0042085 A1 | 2/2010 | Hennings et al. |
| 2010/0049098 A1 | 2/2010 | Shalgi et al. |
| 2010/0066918 A1 | 3/2010 | Gupta et al. |
| 2010/0100014 A1 | 4/2010 | Eshel et al. |
| 2010/0106064 A1 | 4/2010 | Kreindel et al. |
| 2010/0106145 A1 | 4/2010 | Widgerow |
| 2010/0174224 A1 | 7/2010 | Sohn |
| 2010/0185193 A1 | 7/2010 | Kriendel |
| 2010/0185194 A1 | 7/2010 | Kriendel |
| 2010/0198134 A1 | 8/2010 | Eckhouse et al. |
| 2010/0198199 A1 | 8/2010 | Kriendel |
| 2010/0198216 A1 | 8/2010 | Palanker |
| 2010/0204619 A1 | 8/2010 | Rosenberg |
| 2010/0204694 A1 | 8/2010 | Mehta et al. |
| 2010/0217254 A1 | 8/2010 | Mehta |
| 2010/0249772 A1 | 9/2010 | Mehta et al. |
| 2010/0256617 A1 | 10/2010 | Domankevitz et al. |
| 2010/0262135 A1 | 10/2010 | Berube |
| 2010/0293807 A1 | 11/2010 | Bar-El et al. |
| 2011/0015549 A1 | 1/2011 | Eckhouse et al. |
| 2011/0129522 A1 | 6/2011 | MeVorat-Kaplan et al. |
| 2011/0137386 A1 | 6/2011 | Kriendel |
| 2011/0150976 A1 | 6/2011 | Levin et al. |
| 2011/0264173 A1 | 7/2011 | Flyash et al. |
| 2011/0190745 A1 | 8/2011 | Uebelhoer et al. |
| 2011/0218525 A1 | 9/2011 | Hennings et al. |
| 2011/0251527 A1 | 10/2011 | Kushculey et al. |
| 2011/0270364 A1 | 11/2011 | Kriendel et al. |
| 2012/0004548 A1 | 1/2012 | Eshel et al. |
| 2012/0022504 A1 | 1/2012 | Haim et al. |
| 2012/0022627 A1 | 1/2012 | Rosenberg |
| 2012/0136280 A1 | 5/2012 | Rosenberg et al. |
| 2012/0136282 A1 | 5/2012 | Rosenberg et al. |
| 2012/0123397 A1 | 6/2012 | Haim et al. |
| 2012/0143178 A9 | 6/2012 | Mehta |
| 2012/0150079 A1 | 6/2012 | Rosenberg |
| 2012/0150168 A1 | 6/2012 | Rosenberg |
| 2012/0157838 A1 | 6/2012 | Adanny et al. |
| 2012/0158100 A1 | 6/2012 | Schomacker |
| 2012/0172869 A1 | 7/2012 | McGill et al. |
| 2012/0197242 A1 | 8/2012 | Rosenberg |
| 2012/0270743 A1 | 10/2012 | Weisgerber et al. |
| 2012/0271219 A1 | 10/2012 | Weisgerber et al. |
| 2012/0277587 A1 | 11/2012 | Adanny et al. |
| 2012/0310311 A1 | 12/2012 | Elkah |
| 2013/0023855 A1 | 1/2013 | Hennings et al. |
| 2013/0041308 A1 | 2/2013 | Hennings et al. |
| 2013/0072914 A1 | 3/2013 | Domankevitz et al. |
| 2013/0123629 A1 | 5/2013 | Rosenberg et al. |
| 2013/0150841 A1 | 6/2013 | Schomacker et al. |

(56) References Cited

U.S. PATENT DOCUMENTS

| | | |
|---|---|---|
| 2013/0178764 A1 | 7/2013 | Eckhouse et al. |
| 2013/0211347 A1 | 8/2013 | Arbel et al. |
| 2013/0218146 A1 | 8/2013 | Hennings et al. |
| 2013/0226075 A1 | 8/2013 | Hennings et al. |
| 2013/0261436 A1 | 10/2013 | Hennings et al. |
| 2013/0261437 A1 | 10/2013 | Hennings et al. |
| 2013/0261454 A1 | 10/2013 | Hennings et al. |
| 2013/0274841 A1 | 10/2013 | Eckhous et al. |
| 2013/0310714 A1 | 11/2013 | Eshel et al. |
| 2014/0005658 A1 | 1/2014 | Rosenbergr |
| 2014/0025062 A1 | 1/2014 | Rosenberg et al. |
| 2014/0081250 A1 | 3/2014 | Eckhouse et al. |
| 2014/0200564 A1 | 7/2014 | Schomacker et al. |
| 2014/0214022 A1 | 7/2014 | Adanny et al. |
| 2014/0221990 A1 | 8/2014 | Kreindel |
| 2014/0228834 A1 | 8/2014 | Adanny et al. |
| 2014/0249522 A1 | 9/2014 | Adanny et al. |
| 2014/0296852 A1 | 10/2014 | Adanny et al. |
| 2015/0032092 A1 | 1/2015 | Addany |
| 2015/0250543 A1 | 9/2015 | Israeli et al. |
| 2015/0265492 A1 | 9/2015 | Eckhouse et al. |
| 2015/0283026 A1 | 10/2015 | Rosenberg |
| 2015/0328474 A1 | 11/2015 | Flyash et al. |
| 2015/0366611 A1 | 12/2015 | Rosenberger et al. |
| 2016/0045265 A1 | 2/2016 | Bhawalkar et al. |
| 2016/0143692 A1 | 5/2016 | Shang et al. |
| 2016/0367830 A1 | 12/2016 | Eisenmann |
| 2017/0014174 A1 | 1/2017 | Levine et al. |
| 2017/0136237 A1 | 5/2017 | Rosenberg et al. |
| 2017/0266457 A1 | 9/2017 | Eckhouse et al. |
| 2017/0304641 A1 | 10/2017 | Eisenmann et al. |

FOREIGN PATENT DOCUMENTS

| | | |
|---|---|---|
| AU | 2002307781 | 1/2007 |
| AU | 2006209047 | 5/2012 |
| AU | 2011292747 | 3/2014 |
| BR | PI0606804 | 1/2006 |
| CA | 2610757 | 12/2006 |
| CA | 2696227 | 4/2009 |
| CA | 2704740 | 4/2009 |
| CA | 2704164 | 5/2009 |
| CA | 2747767 | 9/2010 |
| CA | 2356175 | 10/2011 |
| CA | 2349169 | 8/2012 |
| CN | 200680003537.7 | 1/2006 |
| CN | 200780008298.9 | 7/2007 |
| CN | 101232852 | 7/2008 |
| CN | 200880019693.1 | 6/2013 |
| CN | 200880101512.X | 6/2013 |
| EP | 0569670 A2 | 11/1993 |
| EP | 1140280 | 12/1999 |
| EP | 2272455 | 9/2001 |
| EP | 1502622 | 4/2002 |
| EP | 2286751 | 3/2003 |
| EP | 1320333 | 6/2003 |
| EP | 1850781 | 1/2006 |
| EP | 2527005 | 2/2007 |
| EP | 1852060 A1 | 11/2007 |
| EP | 1863569 | 12/2007 |
| EP | 1888001 | 12/2007 |
| EP | 2200666 | 10/2008 |
| EP | 2205967 | 10/2008 |
| EP | 2211918 | 10/2008 |
| EP | 1502622 | 6/2009 |
| EP | 2393444 | 2/2010 |
| EP | 2401026 | 2/2010 |
| EP | 2730313 | 2/2010 |
| EP | 2319445 | 9/2010 |
| EP | 2319577 | 5/2011 |
| EP | 2394594 | 12/2011 |
| EP | 2139560 | 5/2012 |
| EP | 2205967 | 5/2013 |
| EP | 2190525 | 7/2013 |
| EP | 2605718 | 3/2014 |
| EP | 1499255 | 7/2015 |
| EP | 1955731 | 8/2015 |
| EP | 1128870 | 8/2016 |
| EP | 1450876 | 8/2016 |
| FR | 1502622 | 4/2002 |
| FR | 1320333 | 6/2003 |
| GB | 1320333 | 6/2003 |
| IL | 181112 | 8/2005 |
| IL | 188968 | 7/2006 |
| IL | 202907 | 1/2007 |
| IL | 193497 | 2/2007 |
| IL | 143014 | 9/2007 |
| IL | 187608 | 11/2007 |
| IL | 202558 | 6/2008 |
| IL | 206652 | 12/2008 |
| IL | 206654 | 12/2008 |
| IL | 213561 | 6/2011 |
| IL | 158582 | 2/2012 |
| IL | 219219 | 4/2012 |
| IL | 184869 | 5/2012 |
| IL | 226319 | 5/2013 |
| IL | 203339 | 7/2014 |
| IL | 200992 | 8/2014 |
| IL | 204969 | 3/2015 |
| JP | 4745500 | 5/2000 |
| JP | 2008-515379 | 5/2008 |
| JP | 4837723 | 8/2008 |
| JP | 4262985 | 2/2009 |
| JP | 2009-527269 A | 7/2009 |
| JP | 4335522 | 7/2009 |
| JP | 4382991 | 10/2009 |
| JP | 4452511 | 2/2010 |
| JP | 2010-528803 | 8/2010 |
| JP | 4638130 | 12/2010 |
| JP | 550702/2011 | 6/2011 |
| JP | 2011-237691 | 11/2011 |
| JP | 5116488 | 10/2012 |
| JP | 2012-542684 | 4/2013 |
| JP | 5294852 | 6/2013 |
| JP | 2013-538323 | 10/2013 |
| JP | 5389025 | 10/2013 |
| JP | 5466161 | 1/2014 |
| JP | 5508272 | 3/2014 |
| JP | 5612474 | 9/2014 |
| JP | 5620458 | 9/2014 |
| JP | 5934211 | 5/2016 |
| KR | 10-2007-0116253 | 12/2007 |
| KR | 10-2008-0025028 | 3/2008 |
| KR | 10-2010-0044161 | 4/2010 |
| KR | 10-2010-0065297 | 6/2010 |
| KR | 10-2012-0037011 | 4/2012 |
| KR | 2012-0111725 | 10/2012 |
| KR | 10-1227286 | 1/2013 |
| KR | 10-1246980 | 3/2013 |
| KR | 10-1272372 | 5/2013 |
| KR | 2013-0128391 | 11/2013 |
| KR | 1679467 | 11/2016 |
| WO | WO 00/38781 | 7/2000 |
| WO | WO 01/085234 | 11/2001 |
| WO | WO 02/092163 | 11/2002 |
| WO | WO 2007013072 | 2/2007 |
| WO | WO 2007093998 | 8/2007 |
| WO | WO 2008091625 | 7/2008 |
| WO | WO 2008152630 | 12/2008 |
| WO | WO 2009/057112 | 5/2009 |
| WO | WO 2010097790 | 9/2010 |
| WO | WO 2010115196 | 10/2010 |
| WO | WO 2011067771 | 6/2011 |
| WO | WO 2012011098 | 1/2012 |
| WO | WO 2012023129 | 2/2012 |
| WO | WO 2012/063236 | 5/2012 |
| WO | WO 2014/141229 | 9/2014 |
| WO | WO 2017130185 | 8/2017 |

METHOD AND APPARATUS FOR FRACTIONAL SKIN TREATMENT

CROSS-REFERENCE TO RELATED REFERENCES

This application is a continuation of U.S. application Ser. No. 14/252,832, filed on Apr. 15, 2014, now issued as U.S. Pat. No. 9,072,882, which is a continuation of U.S. application Ser. No. 13/400,434, filed on Feb. 20, 2012, which is a continuation of U.S. application Ser. No. 12/505,576, filed on Jul. 20, 2009, now issued as U.S. Pat. No. 8,357,150. The contents of these priority applications are incorporated herein by reference. This application is related to U.S. application Ser. No. 12/324,932, filed Nov. 28, 2008, now issued as U.S. Pat. No. 8,216,215, which is incorporated herein by reference.

TECHNOLOGY FIELD

The method and apparatus generally relate to skin treatment procedures and in particular to cosmetic skin resurfacing and rejuvenation procedures.

BACKGROUND

Fractional skin resurfacing or rejuvenation is a recently developed skin ablative technology. There are two types of devices used to ablate the skin: laser based devices and RF based devices. Both types of these devices ablate a pattern of extremely small diameter shallow holes or zones. The holes are microscopically small treatment zones surrounded by untreated skin areas. The treatment results in a very rapid healing or recovery and skin resurfacing of the treated. In the healing process of the treated zones, a layer of new skin appears, restoring a fresh, youthful complexion.

The pattern of small holes is typically produced by an X-Y scanning laser beam or by application of RF energy or voltage. The laser is focused on the skin and usually operates in pulse mode ablating micron size holes in the skin.

RF based fractional skin treatment produces a scanning pattern of micron size holes in the skin a similar to laser. Typically, the energy is delivered to the skin by an applicator equipped by a tip having a plurality of voltage to skin applying/delivering elements or contact elements arranged in a matrix or in an array. The voltage to skin applying elements are placed in contact with the segment of the skin to be treated and driven by a source of suitable power and frequency RF energy. Application of a high voltage RF pulse to the electrodes ablates the skin under the respective electrode forming a small hole.

In some instances application of laser or RF voltage pulses causes discomfort and even pain to the treated subject, although the experience based on the individual and as such, the pain sensation may be different from subject to subject. In other instances there may be a difference in the size of micro holes formed by the applicator at the same treatment session. Healing of larger size holes may take a longer period of time than the healing process for smaller size holes and in some instances, the larger holes may tend to result in causing damage to the skin rather than producing the desired skin effect.

In order to soften the discomfort and lessen the pain and other side effects associated with the fractional treatment, practitioners have started using topically applied lidocaine cream or even oral sedation.

Fractional skin treatment is applicable in the correction of almost all cosmetic skin defects such as signs of aging, wrinkles, discolorations, acne scars, tattoo removal, and other skin defects. The cost of the RF based products is lower than that of the products operating with laser radiation and they will most probably become widely used if the discomfort and occasional pain associated with their use could be eliminated.

US Patent Application Publication No. 2006/0047281 and U.S. patent application Ser. No. 12/324,932 to the same assignee disclose RF based products such as eMatrix™ suitable for fractional skin treatment.

GLOSSARY

In the context of the present disclosure "RF voltage" and "RF energy" are used interchangeably and have the same meaning. The mathematical relationship between these two parameters is well known and knowledge of one of them allows easy determination of the other.

In the context of the present disclosure "skin resistance" and "skin impedance" are used interchangeably and have the same meaning. The mathematical relation between these two parameters is well known and knowledge of one of them allows easy determination of the other.

The term "desired skin effect" as used in the present disclosure means a result of RF energy application, which may be wrinkle removal, hair removal, collagen shrinking or destruction, skin rejuvenation, and other cosmetic and skin treatments.

The term "plateau" of a function is a part of its domain where the function has constant value.

BRIEF SUMMARY

An apparatus for cosmetic RF skin treatment where the RF energy supply is isolated from the subject treated, such that in course of treatment no undesired current flows through the subject body. The apparatus includes an applicator with a tip that is populated by a plurality of voltage applying dome shaped elements protruding from the tip surface and organized in one common cluster and a cluster of electrodes bounding the dome shaped elements and having an area larger than the dome shaped elements have. The apparatus applies voltage to the elements with a magnitude sufficient to cause a desired skin effect. A current limiter limits the RF induced current thereby preventing skin damage. The apparatus continuously senses the treated skin segment impedance and varies the RF energy at a low skin impedance and/or stops the pulse in cases of too low or too high skin impedance.

DETAILED DESCRIPTION OF EXEMPLARY EMBODIMENTS

The principles and execution of the method and the apparatus may be better understood with reference to the drawings and the accompanying description of the non-limiting, exemplary embodiments, shown in the Figures.

Figure 1A:
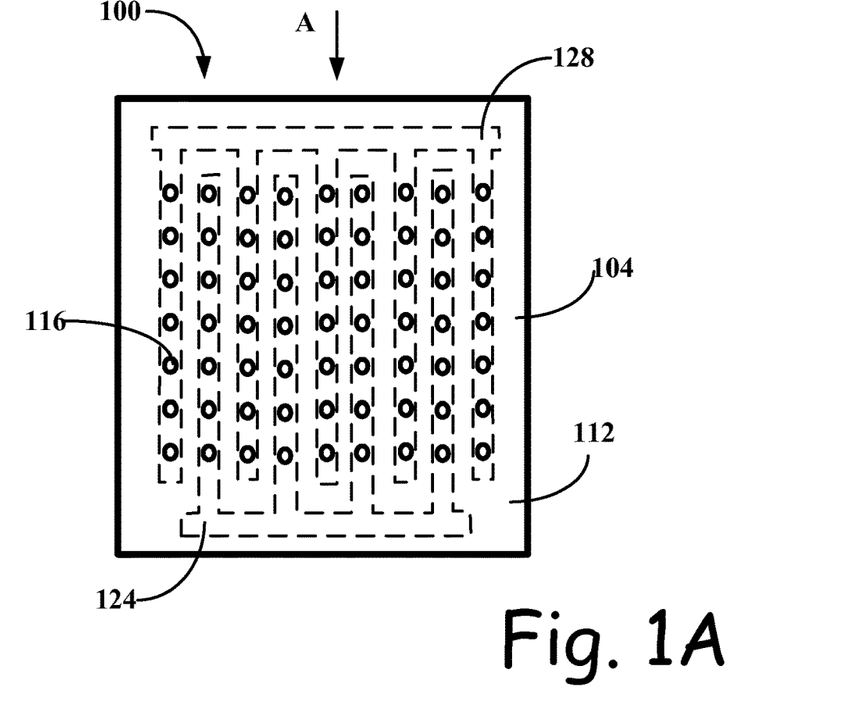
FIGS. 1A and 1B, collectively referred to as FIG. 1, are schematic illustrations of a prior art RF applicator tip for fractional skin treatment.
Figure 1B:
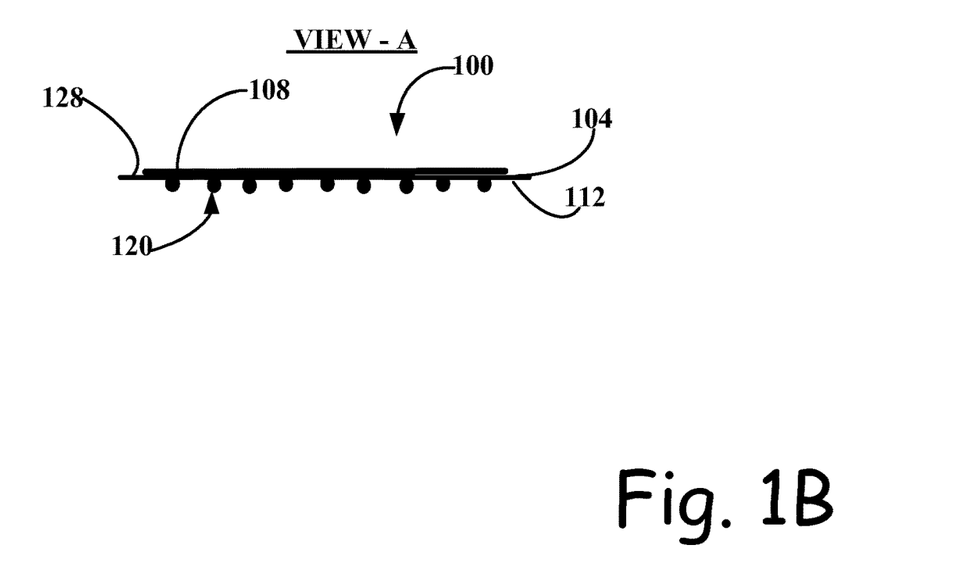

Reference is made to FIG. 1, which is a schematic illustration of a prior art RF applicator tip for fractional skin treatment disclosed in the U.S. patent application Ser. No. 12/324,932 to the same assignee. A carrier 100 on which voltage to skin delivering elements or contact elements are formed may be a flexible or rigid article made of a polyimide film or similar material, with an exemplary thickness range of 0.5 mil to 6 mil (12.5 micron to 150 micron). The term "carrier" in the context of the present disclosure means a substrate having an array of voltage to skin application elements, a two dimensional array or matrix of voltage to skin application elements. Substrate 104 has on one of its surfaces 112 an array or matrix of miniature (microscopic), discrete, voltage to skin application elements 116 protruding from surface 112 and terminated by dome type shapes 120. A pattern of conductors 124 and 128 shown in broken lines arranged on the back or second side of substrate 104 enables addressing of all elements 116, a cluster of elements 116, or each of elements 116 individually. Carrier 100, having formed on it, the voltage to skin delivering elements is configured to allow quick attachment to an applicator and will be termed in the present document as a "tip" or an "applicator tip." An arrangement of RF contacts enabling connection to a source of radio frequency voltage is provided by forming on the back side of the carrier 104 contact points or strips 108 communicating with respective contact arrangements made in substrate 104. Voltage to skin delivering elements 116 are arranged in a symmetric pattern with all even rows 124 connected to one of the RF supply contact strips or ports 124 and all uneven rows 128 connected to another or second contact strip or RF supply port 128.

Figure 2:
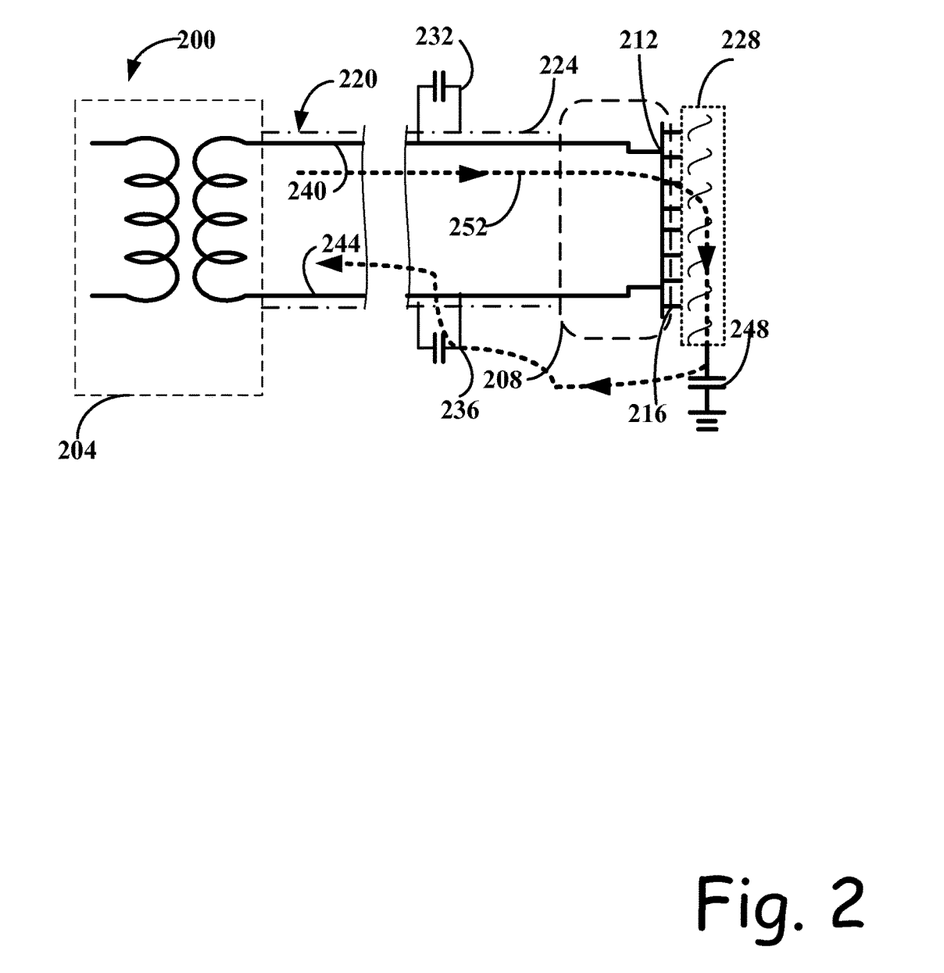
FIG. 2 is a schematic illustration of a prior art RF voltage supplying circuit for driving the RF applicator tip for fractional skin treatment.

FIG. 2 is a schematic illustration of a prior art RF voltage supplying circuit for driving the RF applicator tip for fractional skin treatment. A source of RF voltage 200 may be located in stand alone housing 204. Alternatively, the source of the RF voltage may be located in the applicator case 208 shown in broken lines. The source provides RF voltage to applicator tip 212, and in particular to voltage to skin delivering elements 216 through a shielded harness 220. Shield 224 is schematically shown in broken and doted lines. The length of the harness 220 is selected to enable convenient caregiver operation and may be one to two meters long, for example. There exists a certain parasitic capacitance 232 and 236 between the shield 224 and each of the RF current conducting lines 240 and 244. The treated subject has also certain capacitance 248. For skin treatment, tip 212 is placed in contact with a segment of the skin 228 to be treated. As a result of uneven contact of the voltage to skin delivering elements 216 organized into even 124 and uneven 128 rows or clusters with segment of the skin 228 to be treated, an undesired RF current path 252 may be formed. This current passes through the subject 228 and may cause a painful sensation and even an electric shock to the subject.

Figures 3A, 3B, 3C:
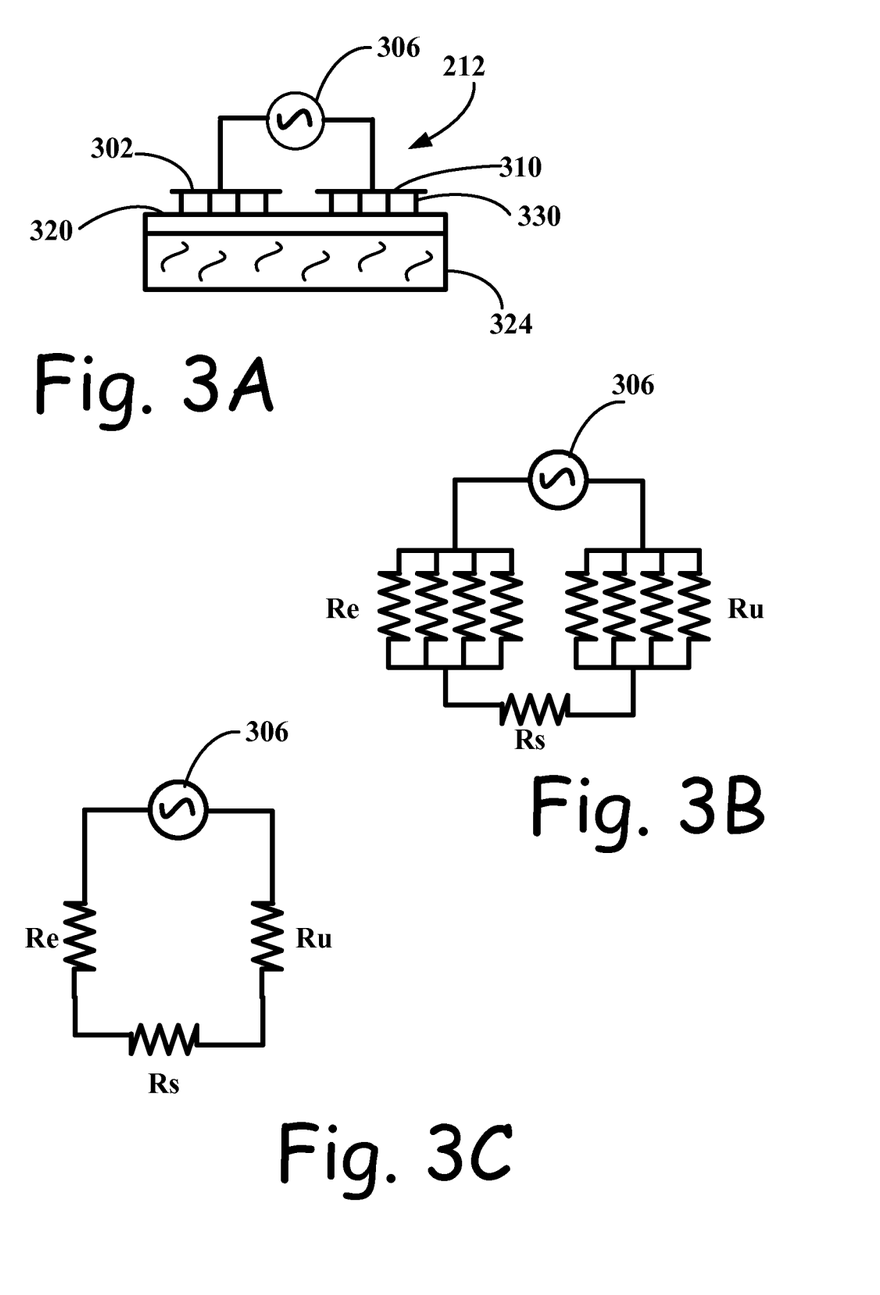
FIGS. 3A through 3C are schematic illustrations of an equivalent electric circuit of the tip for fractional skin treatment.

FIG. 3 is a schematic illustration of an equivalent electric circuit of the tip for fractional skin treatment 212 being in contact with the treated segment of the skin. FIG. 3A schematically shows the tip 212 with all contact elements 330 located in uneven rows 1, 3, 5, and 7 of the tip 212 collectively marked as 302 and shown as connected to a first RF port of RF voltage source 306 and all contact elements located in even rows 2, 4, 6, and 8 collectively marked as 310 and shown as connected to a second RF port of RF voltage source 306. All of the contact elements are in contact with the upper skin layer 320 for example, stratum corneum which has a relatively low conductivity, where numeral 324 marks dermis layer and even deeper skin layers that have a relatively high, as compared to stratum corneum, conductivity.

Referring to FIG. 3B, the electrical channel from each contact element through the low conductance skin layer is represented as a resistor (for the simplicity of the explanation channel capacitance is neglected). The high conductivity dermis is represented as a common resistor Rs. Further equivalent electric scheme simplification is shown in FIG. 3C, where all uneven resistors have been replaced by an equivalent resistor Ru and even rows resistors by Re. Typically, each of the individual contact element resistors is 50K-100K Ohms, therefore Ru and Re are about 2K Ohms each, whereas Rs is an order of magnitude smaller, about 200 Ohms and it can be neglected for the purpose of the discussion.

Because not all of the voltage to skin delivering elements or contact elements 330 (FIG. 3A) may be properly attached to the skin and some of them may bear some dirt and other residuals from the previous treatment, and different skin segments may have different resistance, there is a difference in the resistance to current passing through each of the contact elements and accordingly through the clusters (even or uneven clusters) they form. If the RF voltage or energy flows into any of the Ru or Re resistors, it increases its resistance it generates a positive feedback under which the larger resistor gets more energy than the smaller one, its resistance increases more rapidly, therefore it gets even more energy, and so on. The end result is that the one of Ru or Re clusters, which had initially greater value finally takes most of the energy and leaves a different imprint on the skin (for example, only contact elements located in even or uneven rows may leave an imprint). This reduces the efficacy of the treatment and generates undesired skin effects, excessive pain, and even electric shock.

In order to resolve this problem, as disclosed in the U.S. patent application Ser. No. 12/324,932 assigned to the same assignee, it is possible to address individually each contact element or pin and connect it to the source of voltage through a large impedance, which can be a resistor, a small capacitor, a large inductor, or a combinations of all of them. This would stabilize the RF induced current to each individual channel reducing the "competition" between the contact elements and clusters of contact elements. For sterilization and hygiene purposes use of disposable tips is preferred to the use of reusable tips. Addressing of each individual contact element however, complicates and increases manufacturing cost of such tips.

Another way to equalize the resistance or impedance of each contact element and reduce the pain sensation and potential electric shocks to the treated subject is to bring the skin by some initial treatment to an optimal and more uniform resistance value, which for example may be about 3000 Ohms There will always be however, segments of skin where the resistance is low and any slight sweating may drive the skin to lower impedances.

Figure 4:
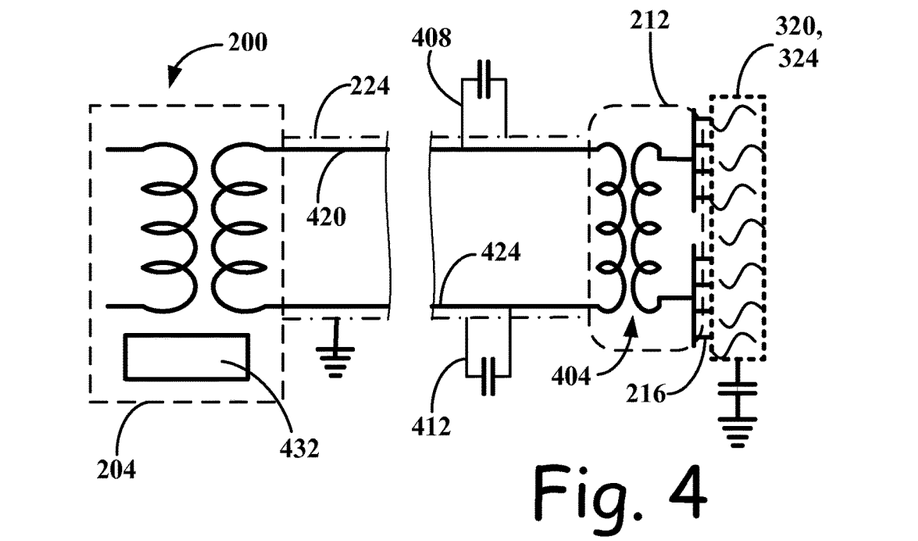
FIG. 4 is a schematic illustration of an exemplary embodiment of the present tip for fractional skin treatment driving circuit.

FIG. 4 is a schematic illustration of an exemplary embodiment of the present tip driving circuit. The embodiment of FIG. 4 eliminates or at least, greatly reduces the pain sensation and electric shock that could affect the treated subject. A low capacitance for example, 4 pF to 10 pF isolating transformer 404 is located in close proximity to the tip 212 with the voltage to skin delivering elements 216. In the course of operation, transformer 404 reduces or completely eliminates currents flowing through the subject body due to parasitic capacitances 408 and 412 formed by the subject skin 320, 324 and the ground and between the shield 224 and each of the RF conducting lines 420 and 424. A controller 432 governing operation of all of the apparatus devices may be located in housing 204. Controller 432 may have a processor, a memory, and other devices necessary for controlling the treatment process.

Figure 5:
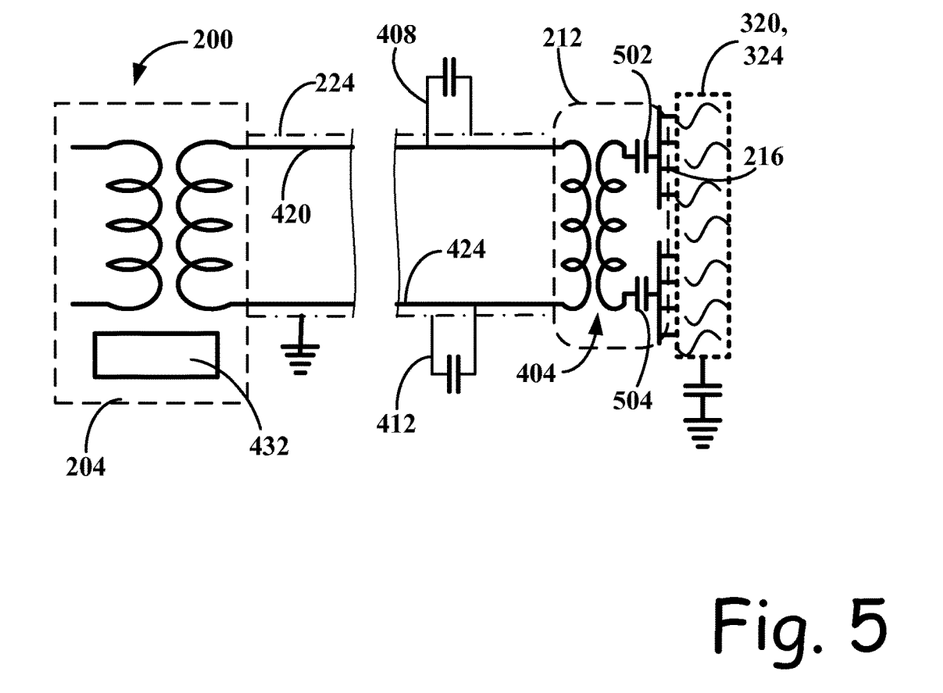
FIG. 5 is a schematic illustration of another exemplary embodiment of the present tip for fractional skin treatment driving circuit.

FIG. 5 is a schematic illustration of an additional exemplary embodiment of the present tip 212 driving circuit that eliminates, or greatly reduces, pain sensation and electric shock that could affect the treated subject. In addition to the low capacitance transformer 404 one or more capacitors 502 and 504 located in the current path and connected in series to the electrodes 216 form a high pass filter. In the course of apparatus operation, the high pass filter filters out the low frequency currents, to which the sensitivity of the treated subject is high, generated by plasma formed at the voltage to skin delivering elements 216 being in contact with the skin 320, 324 and flowing through the subject body in course of the apparatus/applicator operation. (reference can be made to Guidelines for Limiting Exposure to Time-Varying Electric, Magnetic, and Electromagnetic Fields up to 300 GHz; International Commission on Non-Ionizing Radiation Protection, Page 10.

Figure 6:
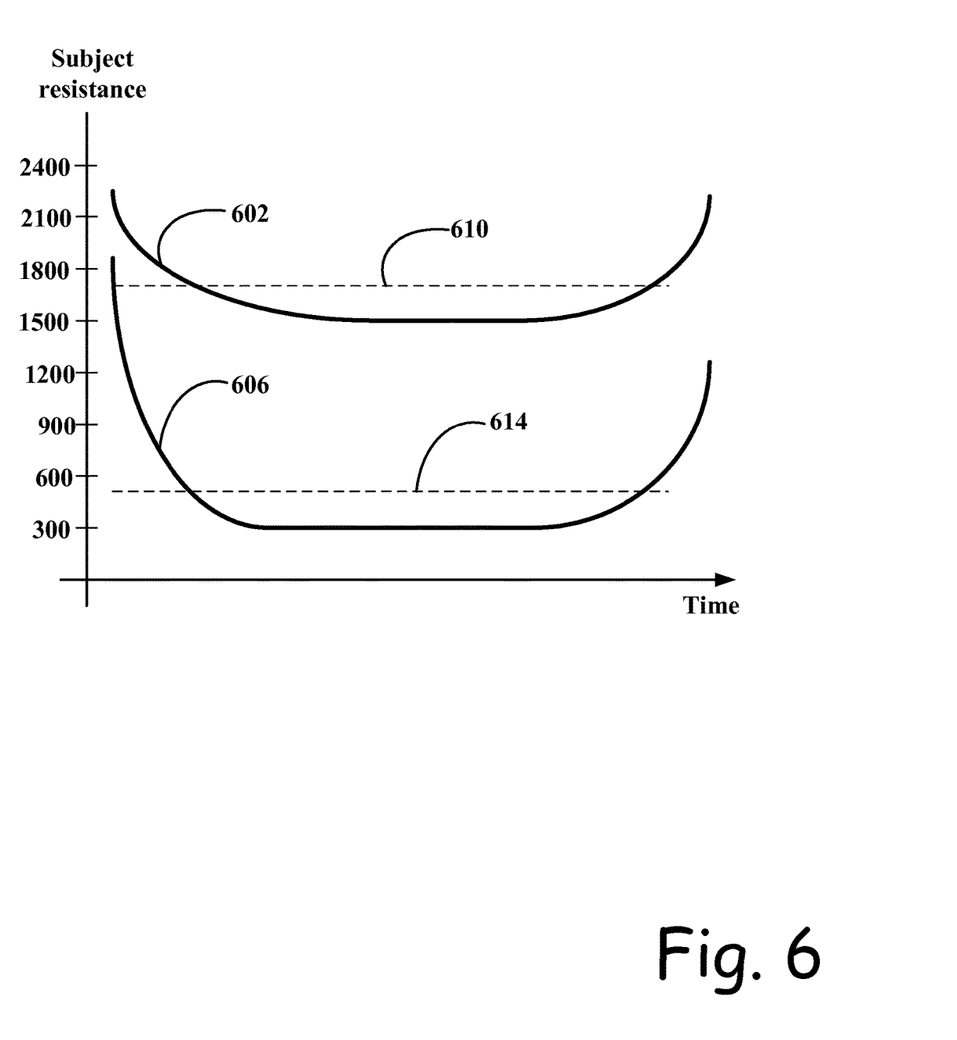
FIG. 6 is a schematic illustration of skin resistance variation under the application of an RF energy pulse.

Electrical resistance of skin differs from subject to subject and complicates proper RF energy value selection and application of the RF energy for cosmetic skin treatment. Further to this, resistance of the subject may vary under application of RF energy. FIG. 6 is a schematic illustration of skin resistance variation under the application of RF energy in a pulse mode. Lines 602 and 606 mark different skin behavior under an RF energy pulse and lines 610 and 614 mark the upper and lower skin resistance or impedance values that result in a desired skin effect, although because of the large variability of the treated subjects skin properties, there may be a need to set experimentally other values matching a particular subject properties. The length of the pulse, as will be explained later, may vary from few milliseconds to hundreds of milliseconds or even seconds.

In order to establish proper treatment parameters prior to the treatment, a system operator or user can calibrate the apparatus and operational treatment parameters derived as a result of the calibration are loaded into a look-up-table (LUT) that may be stored in the memory of the controller 432. For the purpose of calibration, a known variable resistance modeling the subject and the tip behavior is connected instead of a subject to the RF voltage supply. In one of the calibrations, a current flowing in the circuit at different RF voltages and different resistance value is recorded and in another calibration the RF energy applied to the variable resistance, modeling different skin impedance is recorded.

When skin is wet its resistance is low and with the application of the RF energy it continues to fall (line 606). Without being bound by a specific theory it is believed that most of the RF energy applied to the skin is initially wasted to dry the skin and when the skin under the influence of RF energy becomes dry, the skin resistance begins growing to higher values. Resistance increase is believed to be connected with vaporization, accompanied or followed by tissue ablation. It is considered a good treatment (desired skin effect) when ablation is created in the tissue below the electrodes.

It has been experimentally established that treatment resulting in a desired skin effect takes place when the resistance of the subject's skin is between Rlow and Rhigh, where the specific values depend on the number of electrodes in the tip and their arrangement and on the skin properties. For a typical tip shown in FIG. 1, with 64 electrodes and a diameter of 250 μm each, Rlow is about 1500 Ohms and Rhigh is about 4000 Ohms. For the asymmetrical tip of FIG. 8, Rlow is about 600 Ohms and Rhigh is about 1600 Ohms. When the skin resistance (or impedance) falls below the lower limit, most of the RF energy applied to the skin is wasted on drying the skin and not on causing the desired skin effect. Generally, the upper skin resistance limit is in the vicinity of the stratum corneum resistance with the lower limit corresponding to wet skin. When the skin resistance is within the indicated resistance limits, as shown by broken lines 610 and 614, application of RF to the skin through the voltage to skin delivering elements results in a desired skin effect. Continuous or pseudo continuous monitoring of the skin impedance during the RF pulse enables control of the energy delivered to skin. For example, when the resistance falls below the pre-set threshold of e.g. 600 Ohms, the time of the RF pulse may be increased by the control, until the control unit identifies or detects the beginning of an increase in the resistance. From the time that the beginning of the resistance increase is detected, the amount of energy delivered is either fixed or it takes into consideration the energy delivered up to that point, thereby allowing or ensuring the proper skin effect. It is also possible to cut off the RF pulses when the skin impedance is below a pre-set impedance or resistance value and notify operator, to exclude inefficient pulses. Another possibility is to notifying the operator on the low value of skin resistance and the need to dry out the skin. It is also possible to set the apparatus to deliver a pre-set amount of energy to the skin.

It is possible to generalize the skin behavior under an RF pulse into at least two typical cases, although a mixture of these cases and other skin behavior may be present: a) skin resistance remains high through all of the RF pulse application time and b) skin resistance drops down below the lower resistance limit and after it reaches (the function reaches) a plateau it begins to rise. Accordingly, by monitoring the current flowing in the voltage to skin delivering elements circuit, it is possible to set proper treatment parameters resulting in a desired skin effect and not causing adverse side effects such as pain, burnings and other. It was found that resistances above Rhigh correspond to dirty tip and/or are caused by improper attachment of the tip to the skin. In both cases, the pulses may cause undesired pain. In order to reduce the pain, current limiter 704 (FIG. 7) or a control system immediately cuts the pulse when the resistance is above a certain pre-set threshold. The control will notify the operator to check proper attachment of the tip to skin and/or clean the tip.

Figure 7:
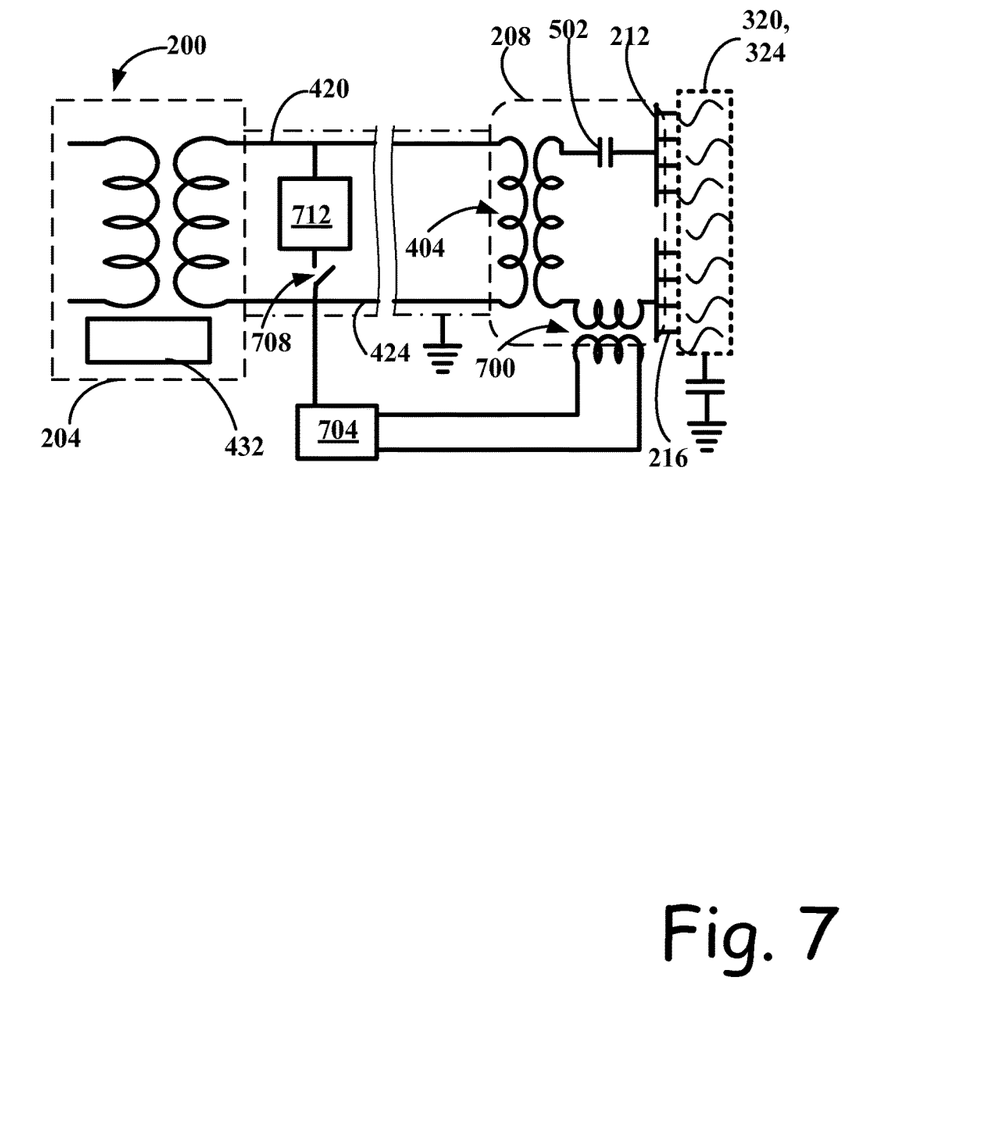
FIG. 7 is a schematic illustration of an exemplary embodiment of the present tip for fractional skin treatment control circuit.

FIG. 7 is a schematic illustration of another exemplary embodiment of the present tip for fractional skin treatment driving circuit that eliminates pain sensation and electric shock that could affect the treated subject. A sensing element 700 senses the current flowing in the immediate to the tip for fractional skin treatment circuit. The sensing and sampling may be continuous or performed at very short time intervals, for example every few tens of a microsecond. A fast response RF induced current limiter 704 in course of operation sets a maximum to the current which flows into the skin. Immediately, with the current increase above a pre-set value, it operates a fast switch 708 that closes the circuit directing the current to an energy absorbing element 712, which dissipates the excessive energy as heat. The RF energy absorbing element 712 may be packaged or even be a part of current limiter 704. The switch may be a bi-polar transistor, a MOSFET switch, an IGBT switch or any other fast switch. If the switch is operated in the analogue regime, it can stabilize the current to the pre-set maximum value or below that value. The energy absorbing element 712 may be a bank of resistors, bridge of diodes or similar devices. This protects the subject from electric shock, skin burn, and other potential treatment side effects.

Figure 8:
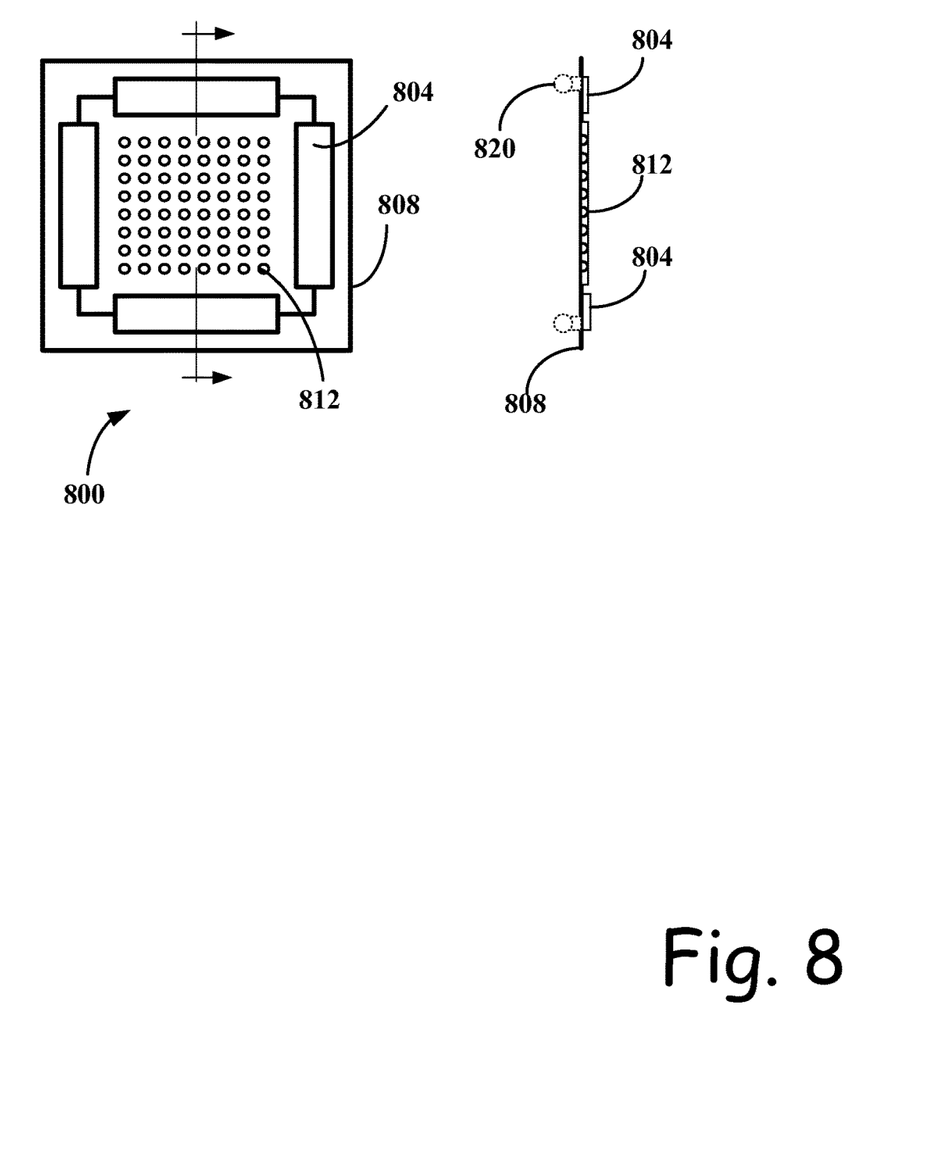
FIG. 8 is a schematic illustration of an exemplary embodiment of the present RF applicator tip for fractional skin treatment.

FIG. 1 illustrates a prior art tip, which is basically a symmetrical tip including even and uneven arrays of electrodes. FIG. 8 is a schematic illustration of an exemplary embodiment of the present RF applicator tip for fractional skin treatment that eliminates or significantly reduces the "competition" between the tip electrodes. Although the tip 800 is for a bi-polar treatment, it is an asymmetrical tip. Tip 800 has one or more (a cluster) large "ground" electrodes 804 located in the peripheral area of substrate 808 and connected to one RF output port. All of the miniature discrete, voltage to skin application elements 812 protruding from the substrate surface and terminated by dome type shapes are connected together to the other port of the RF output transformer. The particular tip has 64 elements, although other designs with different number of elements are possible. The further advantage of this solution is that the resistance variations may be more obvious since there is no competition between the electrodes located in the even and uneven contact strips, thus preventing the undesired partial imprint on the skin and the accompanied pain. The area of the voltage to skin application elements 804 is substantially larger than the area of the terminated by dome type shapes elements 812. Tip 800 possesses a mechanism 820 enabling quick removal and attachment of the tip to the applicator and RF voltage connection elements (not shown).

The electric scheme and the tip structure disclosed above eliminate electrical shock feeling, reduce or eliminate the pain associated with the treatment and increase the treatment efficacy. The isolating transformer is located very close to the application tip to reduce ground currents through parasitic capacitance. Series capacitors located in the path to the electrodes filter out low frequency currents which are produced by plasma formed at the electrodes and fast current limiter sets a maximum to the current which flows into the skin.

Typical operating parameters of the apparatus are:
Voltage on high impedance load: 850 Vp-p
Current: 50-400 mA
Pulse length: 10-150 msec
Energy per pulse (Actual energy delivered to the skin): 0.5-4 J, more typical 1-2 J.
Frequency of the RF: 1 MHz, although 100 kHz up to 10 MHz may be considered.

Typical control parameters for the asymmetrical tip, 64 pins, 250 microns each:
High resistance limit for cutting of pulses for pain reduction: >1600 Ohms (for 64 pins asymmetrical tip)
Low resistance limit for cutting low efficiency pulses: <200 Ohms (for 64 pins asymmetrical tip)
Range of resistance where control adds energy to dry the skin: 200-600 Ohms (for 64 pins asymmetrical tip)

We claim:

1. An RF skin treatment apparatus, comprising:
   an RF voltage source configured to connect to a tip to apply an RF pulse to skin in order to achieve a desired skin effect; and
   at least one processor configured to:
   monitor skin impedance as the RF pulse is applied to the skin;
   compare the monitored skin impedance to a lower threshold, wherein the lower threshold corresponds to an impedance of wet skin; and
   increase a time of the RF pulse when the monitored skin impedance is below the lower threshold until an increase in resistance is detected.

2. The RF skin treatment apparatus of claim 1, wherein the at least one processor is further configured to:
   compare the monitored skin impedance to an upper threshold; and
   a) determine that the monitored skin impedance is below the lower threshold, and provide a wet skin notification to an operator of the skin treatment apparatus indicative of a low value of skin resistance and a need to dry the skin, or
   b) determine that the monitored skin impedance is above the upper threshold, and provide a tip notification to the operator indicative of a need to check for proper attachment of the tip or a need to clean the tip.

3. The RF skin treatment apparatus of claim 2, wherein the at least one processor is further configured to provide a high resistance notification advising the operator of a high value of resistance above the upper threshold when the monitored skin impedance is above the upper threshold.

4. The RF skin treatment apparatus of claim 2, wherein the at least one processor is further configured to cut the RF pulse when the monitored skin impedance is above the upper threshold.

5. The RF skin treatment apparatus of claim 2, wherein at least one of the upper threshold and the lower threshold are chosen to minimize pain to a subject under treatment.

6. The RF skin treatment apparatus of claim 2, wherein the at least one processor is further configured to provide the wet skin notification and the tip notification.

7. The RF skin treatment apparatus of claim 2, wherein the at least one processor is configured to provide the wet skin notification to the operator indicative of the need to dry the skin when the monitored skin impedance is below the lower threshold; and to provide the tip notification to the operator indicative of at least one of the need to check for proper attachment of the tip or the need to clean the tip when the monitored skin impedance is above the upper threshold.

8. The RF skin treatment apparatus of claim 2, further comprising a switch configured to direct current to an energy absorbing element when the monitored skin impedance is above the upper threshold.

9. The RF skin treatment apparatus of claim 1, wherein the desired skin effect includes at least one of wrinkle reduction, hair removal, collagen shrinking, collagen destruction, and skin rejuvenation.

10. The RF skin treatment apparatus of claim 1, wherein the RF voltage source and the at least one processor are configured to cause fractional skin ablation.

11. The RF skin treatment apparatus of claim 1, wherein the RF voltage source and the at least one processor are configured to cause fractional skin treatment.

12. The RF skin treatment apparatus of claim 1, wherein the at least one processor is further configured to provide an inefficient pulse notification advising the operator to exclude inefficient pulses.

13. The RF skin treatment apparatus of claim 1, wherein the at least one processor is further configured to provide a low resistance notification advising the operator of a low value of resistance below the lower threshold when the monitored skin impedance is below the lower threshold.

14. The RF skin treatment apparatus of claim 1, wherein the RF voltage source and the at least one processor are further configured to deliver RF energy to electrodes on the tip.

15. The RF skin treatment apparatus of claim 14, wherein the tip has an asymmetrical electrode arrangement.

16. The RF skin treatment apparatus of claim 15, wherein the asymmetrical electrode arrangement includes at least one electrode having a size greater than a size of another electrode.

17. The RF skin treatment apparatus of claim 15, wherein the asymmetrical electrode arrangement includes a plurality of energy applying electrodes including electrodes of a first size, and at least one larger electrode of a second size located at a periphery of the plurality of energy applying electrodes, the second size being substantially greater than the first size.

18. The RF skin treatment apparatus of claim 17, wherein a combined area of the at least one larger electrode is substantially greater than a combined area of the energy applying electrodes.

19. The RF skin treatment apparatus of claim 14, wherein the RF voltage source and the at least one processor are configured to cause ablation in tissue below the electrodes.

20. The RF skin treatment apparatus of claim 1, wherein the at least one processor is part of a control circuit.

21. The RF skin treatment apparatus of claim 1, wherein the at least one processor is configured to monitor skin impedance by measuring current.

22. The RF skin treatment apparatus of claim 1, wherein the at least one processor is configured to monitor skin impedance by sampling substantially continuously.

23. The RF skin treatment apparatus of claim 1, wherein the at least one processor is configured to monitor skin impedance by sampling every few tens of a microsecond.

* * * * *